United States Patent
Lueken et al.

(10) Patent No.: US 7,154,012 B2
(45) Date of Patent: Dec. 26, 2006

(54) PROCESS FOR PREPARING ALCOHOLS FROM OLEFINS BY HYDROFORMYLATION AND HYDROGENATION

(75) Inventors: Hans-Gerd Lueken, Marl (DE); Alfred Kaizik, Marl (DE); Wilfried Bueschken, Haltern am See (DE); Andreas Stenert, Duelmen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/296,310

(22) Filed: Dec. 8, 2005

(65) Prior Publication Data

US 2006/0129004 A1     Jun. 15, 2006

(30) Foreign Application Priority Data

Dec. 9, 2004     (DE) .................... 10 2004 059 292

(51) Int. Cl.
*C07C 29/14*     (2006.01)
(52) U.S. Cl. ................. 568/881; 568/882; 568/883
(58) Field of Classification Search ................. None
See application file for complete search history.

(56) References Cited

U.S. PATENT DOCUMENTS

| | | | |
|---|---|---|---|
| 4,447,661 A | 5/1984 | Hoshiyama et al. | 568/882 |
| 6,239,318 B1 | 5/2001 | Schuler et al. | 568/881 |
| 6,331,657 B1 * | 12/2001 | Kaizik et al. | 568/882 |
| 6,407,295 B1 * | 6/2002 | Kaizik et al. | 568/883 |
| 6,720,457 B1 * | 4/2004 | Drees et al. | 568/429 |
| 2005/0171389 A1 | 8/2005 | Totsch et al. | 568/909 |

FOREIGN PATENT DOCUMENTS

| | | |
|---|---|---|
| DE | 102 27 995 | 9/2003 |
| DE | 102 27 995 A1 | 9/2003 |
| GB | 1 387 657 | 3/1975 |

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process for preparing aliphatic alcohols that includes cobalt-catalyzed hydroformylation of olefins, treatment of a hydroformylation mixture with oxygen-containing gases in the presence of acidic, aqueous cobalt(II) salt solutions, separation of a mixture into an aqueous phase comprising cobalt salts and an organic phase comprising the aliphatic aldehydes, and hydrogenation of an aldehyde-containing organic phase wherein the organic phase and treatment with an adsorbent to separate off cobalt compounds prior to hydrogenation.

16 Claims, 2 Drawing Sheets

PROCESS FOR PREPARING ALCOHOLS FROM OLEFINS BY HYDROFORMYLATION AND HYDROGENATION

BACKGROUND OF THE INVENTION

1. Field of the Invention

The present invention relates to a process for preparing alcohols by hydroformylation of olefins or olefin mixtures in the presence of a cobalt catalyst, removal of the catalyst and subsequent hydrogenation. The invention further relates to alcohols prepared by the process, and mixtures obtained by the process.

2. Discussion of the Related Art

Higher alcohols, in particular those having from 7 to 25 carbon atoms, may be prepared by catalytic hydroformylation (also known as the oxo process) of the olefins having from 6 to 24 carbon atoms to form aldehydes having from 7 to 25 carbon atoms and subsequent hydrogenation of the aldehydes. The alcohols can be used for many purposes including as solvents or as precursors for detergents or plasticizers.

A large number of processes for the hydroformylation of olefins are known in the literature. U.S. Pat. No. 5,268,514, U.S. Pat. No. 536,912, U.S. Pat. No. 5,462,986 and U.S. Pat. No. 5,463,147 describe the hydroformylation of 1- and 2 butene-containing mixtures, in which the 1-butene is reacted in a heterogeneous reaction, i.e. in a multiphase system, if appropriate with addition of a phase transfer reagent or solubilizer, in the first stage and a homogeneously dissolved catalyst is used in the second stage. In U.S. Pat. No. 5,268,514 and U.S. Pat. No. 536,912, rhodium catalysts are used in both stages, while according to U.S. Pat. No. 5,462,986 and U.S. Pat. No. 5,463,147 rhodium catalysts are used in the first stage and cobalt catalysts are used in the second stage. According to U.S. Pat. No. 5,268,514 and U.S. Pat. No. 536,912, the olefin which is not reacted in the first stage, predominantly 2-butene, is hydroformylated in a homogeneous phase and in the presence of rhodium as catalyst in a second stage. In U.S. Pat. No. 5,462,986 and U.S. Pat. No. 5,463,147, this procedure is defined more precisely in that the olefins which have not reacted in the first stage leave the reactor in gaseous form together with carbon monoxide, hydrogen and butene formed by hydrogenation, i.e. an intermediate separation of the olefins is carried out. The gas which has been separated off is, if appropriate after compression, passed to the second hydroformylation stage.

GB 1 387 657 describes a two-stage hydroformylation in which the reaction product of the first stage is discharged in gaseous form and, after the aldehydes or alcohols have been condensed out, the offgas from the first stage, which comprises unreacted olefins, is partly recycled to the first stage and the other part is passed to a second reactor.

A further variant of a two-stage hydroformylation is described in U.S. Pat. No. 4,447,661. Olefins are hydroformylated to conversions of from 50 to 90% in a first stage using a cobalt catalyst, the cobalt catalyst is separated off from the reaction mixture and the aldehydes formed are introduced together with the unreacted olefins into a second hydroformylation stage. The ligand-modified cobalt catalyst used here brings about not only the hydroformylation of the olefins, but at the same time hydrogenation of the aldehydes to the alcohols.

U.S. Pat. No. 6,482,992 describes a process for the multistage cobalt- or rhodium-catalyzed hydroformylation of olefins having from 6 to 24 carbon atoms to produce alcohols and/or aldehydes, in which the olefins
a) are hydroformylated to a conversion of from 20 to 98% in a hydroformylation step,
b) the catalyst is removed from the liquid reactor output,
c) the liquid hydroformylation mixture obtained in this way is separated into a low-boiling fraction comprising olefins and paraffins and a bottom fraction comprising aldehydes and/or alcohols, the olefins present in the low-boiling fraction are reacted in further process stages comprising the process steps a, b and c, and the bottom fractions of the process steps c) of all process stages are combined.

This process is preferably carried out so that the liquid reactor output from the hydroformylation step a) is a homogeneous liquid phase. The cobalt or rhodium catalysts are preferably used in such a way that they are homogeneously dissolved in the liquid reactor output from the hydroformylation step a).

U.S. Pat. No. 6,331,657 describes a process for preparing higher oxo alcohols from mixtures of isomeric olefins having from 5 to 24 carbon atoms by means of a two-stage hydroformylation in the presence of a cobalt or rhodium catalyst at elevated temperature and superatmospheric pressure, in which the reaction mixture from the first hydroformylation stage is selectively hydrogenated, the hydrogenation mixture is separated in a distillation into crude alcohol and low boilers comprising predominantly olefins, these are fed to the second hydroformylation stage, the reaction mixture from the second hydroformylation stage is once again selectively hydrogenated, the hydrogenation mixture is separated in a distillation into crude alcohol and low boilers, the crude alcohol is worked up by distillation to give pure alcohol and at least part of the low boilers is taken off to discharge saturated hydrocarbons from the system.

The residual amounts of cobalt catalyst remaining in the organic phases obtained after the hydroformylation in the presence of a cobalt catalyst are generally less than 5 ppm of cobalt (calculated as metal). Even these small residual amounts of cobalt can with increasing period of operation have adverse effects both on the hydrogenation and on the work-up by distillation.

The hydrogenation catalysts may be deactivated by the residual cobalt in the organic phase as the period of operation increases. In particular, cobalt deposits on the catalyst surface are observed on prolonged operation.

Apart from the deactivation of the catalyst, the cobalt deposits also have an adverse effect on the hydrodynamics and the mass transfer and/or heat transport in the hydrogenation reactor.

U.S. Pat. No. 6,365,783 discloses a two-stage process for preparing alcohols from olefins or olefin mixtures. In this process, the feed olefin is hydroformylated to an extent of from 50 to 90% in the presence of a cobalt catalyst in the first reaction stage. After the catalyst has been separated off, the unreacted olefins are separated off by distillation from the reaction output and the olefins which have been separated off are reacted in a second hydroformylation reactor. The hydroformylation products from both stages can be hydrogenated to form the corresponding alcohols. In both reaction stages, the catalyst used is $Co_2(CO)_8$ or $HCo(CO)_4$ which is produced outside the hydroformylation reactors. The cobalt catalyst is removed from the reaction mixture from the hydroformylation by extraction with a base prior to further processing.

In most of the cobalt-catalyzed hydroformylation processes known from the literature, the cobalt catalyst (e.g., $HCo(CO)_4$ or $Co_2(CO)_8$) is destroyed by oxidation after the hydroformylation step. This is generally achieved by reacting the output from the hydroformylation with air in the presence of an aqueous phase, with the cobalt(II) salts produced in this way being extracted into the aqueous phase. The aqueous phase is separated off, for example, by decantation in a phase separation vessel or in other apparatuses suitable for this purpose. After the organic phase has been separated off from the aqueous phase, it is passed to a catalytic hydrogenation.

In DE 102 27 995.0, the concentration of cobalt compounds (calculated as metallic cobalt) in the hydroformylation mixtures is reduced to values below 0.5 ppm by mass by extraction with water. The operating life of the hydrogenation catalyst in respect of satisfactory hydrogenation performance can in this way be increased to about 2–3 years. However, a disadvantage which remains is that the first catalyst layer in the hydrogenation of the extracted hydroformylation mixture becomes conglutinated by deposited metallic cobalt and possibly other substances. As a result, an increasing differential pressure builds up in the reactor and the flow of the liquid to be hydrogenated becomes nonuniform in the subsequent catalyst layers, so that the hydrogenation performance decreases. The hydrogenation has to be shut down at intervals for the first catalyst layer to be loosened or be replaced by fresh catalyst.

SUMMARY OF THE INVENTION

To avoid such interruptions to operation with the resulting production downtimes and costs, it is an object of the invention to improve the process of preparing alcohols in such a way that such interruptions have to take place only rarely.

The invention includes a process for preparing aliphatic alcohols having from 7 to 25 carbon atoms, in which the process steps
  a) cobalt-catalyzed hydroformylation of olefins having from 6 to 24 carbon atoms,
  b) treatment of a hydroformylation mixture with oxygen-containing gases in the presence of acidic, aqueous cobalt(II) salt solutions
  c) separation of a mixture obtained according to step b) into an aqueous phase comprising cobalt salts and an organic phase comprising the aliphatic aldehydes and
  d) hydrogenation of an aldehyde-containing organic phase are carried out at least once and at least part of the aldehyde-containing organic phase is treated with an adsorbent in a step e) to separate off cobalt compounds prior to the hydrogenation d).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
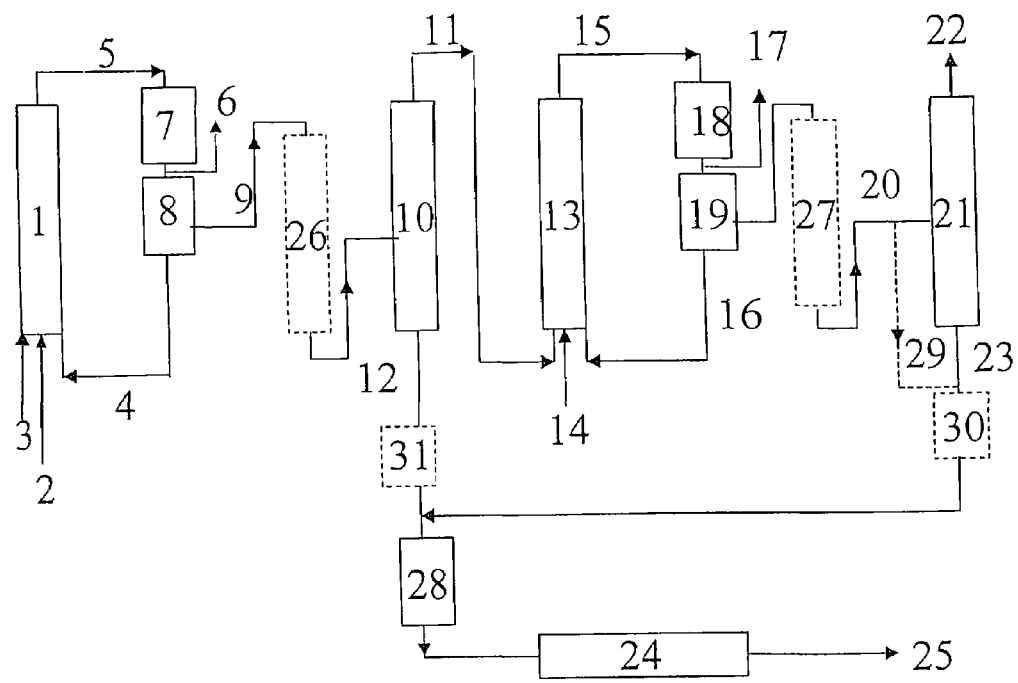
FIG. 1 shows a block diagram of one embodiment of the process for preparing aliphatic alcohols.

It has now been found that the increase in the differential pressure caused by deposits in the first catalyst layer of a hydrogenation reactor can be reduced if the mixture to be hydrogenated flows through an adsorption bed in which cobalt compounds are retained before the mixture enters the hydrogenation reactor.

The invention includes a process for preparing aliphatic alcohols having from 7 to 25 carbon atoms, in which the process steps
  a) cobalt-catalyzed hydroformylation of olefins having from 6 to 24 carbon atoms,
  b) treatment of a hydroformylation mixture with oxygen-containing gases in the presence of acidic, aqueous cobalt(II) salt solutions
  c) separation of a mixture obtained according to step b) into an aqueous phase comprising cobalt salts and an organic phase comprising the aliphatic aldehydes and
  d) hydrogenation of an aldehyde-containing organic phase are carried out at least once and at least part of the aldehyde-containing organic phase is treated with an adsorbent in a step e) to separate off cobalt compounds prior to the hydrogenation d).

The present invention likewise provides an organic phase which comprises an aldehyde having from 7 to 25 carbon atoms and is obtainable as intermediate after carrying out process step e) when carrying out the process of the invention. The present invention further includes aliphatic alcohols prepared by using the invention process.

The process of the invention has the advantage that the cobalt catalyst present in any organic phase can be removed completely or virtually completely by the use of adsorbers. This can prevent an increasing differential pressure from building up and further prevent nonuniform flow occurring in the catalyst layers in the hydrogenation reactor as a result of the deposition of catalyst residues. The costs of procuring replacement charges of catalyst can therefore be limited to the required amount by means of the process of the invention. In addition, the labor costs for the frequent installation of catalysts are saved. Furthermore, production downtimes due to interruptions to operation are avoided by the use according to the invention of the adsorber. Since exhausted hydrogenation catalyst which is no longer suitable as hydrogenation catalyst is also suitable as adsorbent, the operating costs can be reduced further by utilization of the exhausted hydrogenation catalysts as adsorbents.

The process of the invention is described by way of example below without the invention being restricted to the illustrated embodiments. If ranges, general formulae or classes of compounds are indicated below, these are intended to encompass not only the ranges or groups of compounds which are explicitly mentioned but also all subranges and subgroups of compounds which can be obtained by omission of individual values (ranges) or compounds.

In the process of the invention for preparing aliphatic alcohols having from 7 to 25 carbon atoms the following steps are included
  a) cobalt-catalyzed hydroformylation of olefins having from 6 to 24 carbon atoms,
  b) treatment of a hydroformylation mixture with oxygen-containing gases in the presence of acidic, aqueous cobalt(II) salt solutions,
  c) separation of a mixture obtained according to step b) into an aqueous phase comprising cobalt salts and an organic phase comprising the aliphatic aldehydes, and
  d) hydrogenation of an aldehyde-containing organic phase.

In embodiments each of a)–d) are carried out at least once and at least part of the aldehyde-containing organic phase is treated with an adsorbent in a step e) to separate off cobalt compounds prior to the hydrogenation d).

In the process of the invention, it is possible to use all adsorbents which are able to separate off cobalt compounds from an organic phase comprising aldehydes and possibly water, with the restriction that the adsorbents must not catalyze, or catalyze only to an insignificant extent, the conversion of desired products (aldehydes, alcohols and formates thereof) into by-products under the adsorption conditions.

The adsorbents are preferably solid materials which are insoluble in the aldehyde phase and preferably also in water. The adsorbents can include, for example, organic resins having functional groups which can bind cobalt and possibly other metals. The cobalt or other metals can be bound by ion exchange, chelation, other reactions or other coordination.

Another group of materials which can be used as adsorbents in the process of the invention are inorganic solids which are preferably porous and thus have a large surface area. Such inorganic solids can be, for example, activated carbon or titanium dioxide, zirconium dioxide, aluminum oxide, silicon dioxide or aluminosilicates in their various modifications.

Preference is given to using an aluminum oxide ($Al_2O_3$), silicon oxide ($SiO_2$), aluminosilicates or activated carbon, or at least one material comprising these substances as adsorbent. The aluminum oxide, the aluminosilicates and the silicon oxide can be present in all known modifications such as an α, β or γ phase.

It can be advantageous to use exhausted or fresh (hydrogenation) catalysts, particularly preferably exhausted hydrogenation catalysts, as adsorbent. In this way, the catalysts which are no longer suitable for the hydrogenation, e.g. in step d), because of an unsatisfactory activity can be used for removing cobalt from the aldehyde-containing phase, so that the catalysts perform a useful function for a longer period of time. Preference is given to using hydrogenation catalysts comprising aluminum oxide ($Al_2O_3$), silicon oxide ($SiO_2$), aluminosilicates or activated carbon as support materials as adsorbents.

Particular preference is given to using adsorbents which have a large surface area. Preferred adsorbents have BET surface areas of from 80 to 300 $m^2/g$, preferably from 120 to 280 $m^2/g$ and particularly preferably from 180 to 250 $m^2/g$ (determined by the BET method by nitrogen adsorption in accordance with DIN 66 131). Very particular preference is given to using aluminum oxides as adsorbents having a BET surface area of from 80 to 300 $m^2/g$, preferably from 120 to 280 m 2/g and particularly preferably from 180 to 250 $m^2/g$.

The adsorbent is advantageously used in a form in which it offers little resistance to flow, e.g. in the form of granules, pellets or shaped bodies such as tablets, cylinders, rod extrudates or rings.

For the purposes of the present invention, one or more adsorbents can be used for adsorbing the cobalt compounds from the liquid organic phase. For example, an adsorbent can be used in different shapes or sizes. It is also possible to use adsorbents comprising different materials (different chemical composition or different modification).

When at least two different adsorbents are used, these can be present in mixed form or in layers in the adsorber. When a plurality of adsorbers is used, the individual adsorbers can contain identical or different adsorbents or mixtures thereof.

Furthermore, the adsorbent can further comprise inert materials such as glass spheres. The adsorbent can then be diluted by means of these glass spheres. This has the advantage that the risk of conglutination of the particles of the adsorbent is reduced, the formation of local regions of overheating (hot spots) is avoided and the differential pressure in the adsorption vessel may be able to be reduced. The adsorbents can optionally contain from 0.01 to 2% by mass of basic substances, for example compounds of the alkali metals, of the alkaline earth metals or of zinc.

Step e) (the adsorption) can be carried out batchwise or continuously, e.g. in stirred vessels or flow reactors. In the process of the invention, the adsorption is preferably carried out continuously over particulate adsorbents in flow reactors (flow tubes).

Step e) is preferably carried out at a temperature in the range from 5 to 250° C., more preferably from 10 to 100° C., particularly preferably from 15 to 75° C. and particularly preferably from 20 to 50° C. The pressure at which the step e) in the process of the invention is carried out is preferably from 0.1 to 20 MPa, more preferably from 0.1 to 5 MPa and particularly preferably from 0.2 to 0.5 MPa.

As adsorber, i.e. an apparatus in which step e) can be carried out, it is possible to employ customary closed industrial vessels having an inlet and outlet at positions located opposite one another on the vessel. In the process of the invention, particular preference is given to using tube reactors as adsorbers. These can be operated in the recirculation mode or preferably in a single pass. Flow through vertical tube reactors can be from the bottom upward or vice versa. Flow from the top downward is preferred in the process of the invention.

The superficial velocity in the adsorber is preferably in the range from 10 m/h to 300 m/h, more preferably in the range from 50 m/h to 150 m/h and particularly preferably in the range from 75 to 120 m/h. The space velocity (LHSV) over the adsorbent (volume of organic phase in liter per liter of adsorbent per hour) is dependent on the adsorbent used and the cobalt concentration in the inflowing liquid. For example, in the case of a cobalt concentration of from 50 to 150 ppb by mass and γ-aluminum oxide as adsorbent, the LHSV is preferably in the range from 40 $h^{-1}$ to 80 $h^{-1}$.

The adsorption according to the invention in step e) can be carried out with or without addition of hydrogen. In particular, the step e) can be carried out within or outside a reactor in which a hydrogenation according to step d) is carried out. If the adsorption is carried out in the presence of hydrogen, the adsorber is preferably integrated into the hydrogenation reactor. This can be achieved, for example, by the hydrogenation reactor having two zones, viz. one zone which is equipped with the hydrogenation catalyst and a zone which is provided with the adsorbent, with the zone containing the adsorbent being located between the inlet into the reactor and the zone containing the hydrogenation catalyst. The advantage of this is that an apparatus is saved. However, it results in the disadvantage that the hydrogenation has to be interrupted when the adsorbent is changed. It is therefore better to carry out the adsorption outside the hydrogenation reactor.

The adsorption of the cobalt compounds can be carried out in one or more adsorber(s). When only one adsorber outside the hydrogenation reactor is used, there is a choice between shutting down the hydrogenation and passing an increased amount of cobalt over the hydrogenation catalyst when the adsorbent is changed. Both are disadvantageous.

For this reason, the step e) in the process of the invention is preferably carried out using at least two adsorbers, because it is then possible to continue the hydrogenation without additional exposure of the catalyst to cobalt compounds when one adsorber is taken out of operation to allow the adsorbent to be changed or regenerated.

If more than one adsorber is present for carrying out the step e) in the process of the invention, these can be connected to one another in different ways, namely in series, in parallel or, if more than two adsorbers are present, in a combination of the two ways. If all adsorbers are connected in series, each adsorber has to be provided with a bypass so that the step e) does not have to be interrupted when one adsorber is taken out of operation.

Step e) is preferably carried out in an apparatus in which at least two adsorber units connected in parallel. These can be operated simultaneously or preferably alternately. Each adsorber unit can comprise one or more adsorber(s). It is also possible for more than two adsorber units to be connected in parallel. When adsorber units connected in parallel are employed, the adsorbent in the adsorber unit which is not currently in operation can be replaced or regenerated.

When carrying out the process step e), an adsorber may be preferably taken out of operation at the latest when the capacity limit for the uptake for cobalt compounds has been reached. Another reason for taking an adsorber out of operation can be an increase in the differential pressure between inlet and outlet of an adsorber.

After an adsorber has been taken out of operation, the adsorbent in the adsorber can be regenerated or replaced by fresh adsorbent. In the process of the invention, the adsorbent is preferably replaced. The cobalt-laden adsorbent which has been replaced can be worked up, recycled or disposed of.

The operating life of the hydrogenation catalyst in step d) can be increased by means of the process of the invention, since cobalt compounds and also other metal compounds, in particular those of iron and of nickel, can be removed from the hydrogenation feed to step e). Furthermore, the buildup of a differential pressure over the first catalyst layer can be reduced. This makes it possible to operate the hydrogenation without interruption over a revision period (5 years).

In the process of the invention, the removal of traces of cobalt compounds in step e) is carried out by means of adsorption. Depending on the cobalt content of the organic phase to be treated in step e), the removal of cobalt compounds can be effected by adsorption alone or else by means of a combination of extraction (step g)) and adsorption (step e)). Here, the extraction is the first stage. The two-stage removal in which part of the cobalt is removed from the mixture fed to step e) by single or multiple extraction with water in a preceding step g) is the preferred embodiment of the present invention. In the process of the invention, it is not necessary for an adsorption stage to be present between each individual extraction stage, but it is important that all of the organic stream fed to the hydrogenation reactor has passed through at least one adsorption stage (step e)).

The method of carrying out step g) can be taken from the prior art. The reduction of the residual cobalt content of decatalyzed hydroformylation mixtures by extraction is described, for example, in the patent application DE 102 27 995. The extraction of which is incorporated herein as a possible embodiment of step g) into the disclosure of the present application by reference.

In DE 102 27 995, the concentration of cobalt compounds (calculated as metallic cobalt) is reduced to preferably below 0.5 ppm by mass by extraction of the organic phase with water, preferably continuously in countercurrent in conventional industrial extractors. Organic streams having such low cobalt concentrations are preferably fed to the step e).

The use of step e) according to the invention, if appropriate together with a prior treatment according to step g) enables the cobalt content of the organic phase which is to be fed to the hydrogenation of step d) to be reduced to preferably less than 30 ppb by mass (30*10-9), more preferably less than 20 ppb by mass and particularly preferably less than 10 ppb by mass. An organic phase comprising at least one aldehyde having from 7 to 25 carbon atoms is obtained as an intermediate of the process of the invention after carrying out process step e). This aldehyde-containing organic phase has a cobalt content as just indicated.

Apart from the adsorption step e), the process of the invention comprises, as described above, the steps a) to d). These can be carried out as described in the prior art or below.

In the process of the invention, olefins or mixtures of olefins having from 6 to 24 carbon atoms, preferably from 8 to 16 carbon atoms and particularly preferably from 8 to 12 carbon atoms, or mixtures comprising such olefins can be used as starting materials. The mixtures can comprise olefins having terminal and/or internal C—C double bonds. The mixtures can comprise or consist of olefins having an identical, similar (±2) or significantly different (>±2) number of carbon atoms. Examples of olefins which can be used as feed either in pure form, in a mixture of isomers or in a mixture with further olefins having a different number of carbon atoms are: 1-, 2- or 3-hexene, 1 heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctene, 1-, 2-, 3-, 4 or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Further suitable starting materials are, inter alia, the mixture of isomeric hexenes obtained in the dimerization of propene (dipropene), the mixture of isomeric octenes obtained in the dimerization of butenes (dibutene), the mixture of isomeric nonenes obtained in the trimerization of propene (tripropene), the mixture of isomeric dodecenes obtained in the tetramerization of propene or the trimerization of butenes (tetrapropene or tributene), the hexadecene mixture obtained in the tetramerization of butenes (tetrabutene) and also olefin mixtures prepared by cooligomerization of olefins having differing numbers of carbon atoms (preferably from 2 to 4), if appropriate after fractional distillation to produce fractions having an identical or similar (±2) number of carbon atoms. Furthermore, it is possible to use olefins or olefin mixtures which have been produced by the Fischer-Tropsch synthesis. Olefins which have been prepared by olefin metathesis or by other industrial processes can also be used. Preferred starting materials are mixtures of isomeric octenes, nonenes, dodecenes or hexadecenes, i.e. oligomers of lower olefins such as n-butenes, isobutene or propene. Other starting materials which are likewise well suited are oligomers of $C_5$-olefins, e.g. mixtures of isomeric decenes.

There are in principle at least three process variants for the oligomerization of butenes to produce essentially $C_8$-olefin-containing mixtures. The oligomerization over acid catalysts has long been known, with, for example, zeolites or phosphoric acid on supports being used industrially. This gives isomer mixtures of branched olefins which are essentially dimethylhexenes (WO 92/13818). A process which is likewise practised worldwide is oligomerization using soluble Ni complexes, known as the Dimersol process (cf. J. Schulze, M. Homann, "$C_4$-Hydrocarbons and Derivates", Springer-Verlag, Berlin, Heidelberg 1989, p. 69 and B. CORNILS, W. A. HERMANN, "Applied Homogeneous Catalysis with Organicmetallic Compounds", Vol. 1&2, VCH, Weinheim, New York 1996), incorporated herein by reference. The third process variant is the oligomerization over fixed-bed nickel catalysts; one of the processes is the Octol process (Hydrocarbon Process., Int. Ed. (1986) 65 (2. Sect. 1) pages 31–33), incorporated herein by reference, in which nickel catalysts as described in U.S. Pat. No. 5,177,282 are used, incorporated herein by reference. For the preparation according to the invention of a C9-alcohol mixture which is suitable, in particular, for the preparation of plasticizers, preference is given to using a C8-olefin mixture which has been obtained from linear butenes by the Octol process.

a) Hydroformylation Reaction

The hydroformylation of the olefins in step a) in the process of the invention is carried out in the presence of one or more cobalt catalysts, preferably unmodified catalysts such as $HCo(CO)_4$ and/or $Co_2(CO)_8$, and of water. The hydroformylation reaction can be carried out using either a preformed catalyst or a catalyst precursor, e.g. a cobalt compound, from which the actual catalyst is formed in the reactor.

If the finished, active catalyst (e.g. $HCo(CO)_4$ and/or $CO_2(CO)_8$) is used, water, olefin, synthesis gas and the active catalyst are fed into the reactor in which the hydroformylation is carried out. Water can be dispersed in the olefin upstream of the reactor, for example by use of a static mixer. However, it is also possible to mix all components only in the reactor.

The amount of water in the hydroformylation reactor can be varied within a wide range. Water can be homogeneously dissolved or additionally dispersed in the liquid hydroformylation output by setting of the ratio of water and olefin and the reaction parameters, for example the temperature.

In the process of the invention, the catalyst ($HCo(CO)_4$ and/or $Co_2(CO)_8$) is preferably generated in the hydroformylation reactor in step a). Such a hydroformylation procedure is described, for example, in U.S. Pat. No. 6,015,928, incorporated herein by reference. In this way of carrying out the process, the starting materials, viz. the cobalt salt solution, the organic phase and the synthesis gas, are introduced simultaneously, preferably with the aid of a mixing nozzle, in cocurrent into the reactor from below.

As cobalt compounds, preference is given to using cobalt salts such as formates, acetates or salts of carboxylic acids which are soluble in water. Cobalt acetate has been found to be particularly useful and is used as an aqueous solution having a cobalt content of from 0.5 to 3% by mass, preferably from 0.8 to 1.8% by mass, calculated as metal. A further preferred starting solution for the preparation of the catalyst is the aqueous cobalt salt solution obtained in the separation step c).

The amount of water which is wanted in the hydroformylation reactor can be introduced with the cobalt salt solution whose concentration can be varied within a wide range. However, it is also possible to feed in additional water in addition to the cobalt salt solution.

In the cobalt-catalyzed process, particular importance should be attached to the metering of the starting materials into the reactor. The metering device should ensure good mixing of the phases and generation of a very high exchange area between the phases. It can also be advantageous to divide the reactor volume of the hydroformylation reactors by installation of from 1 to 10, preferably from 2 to 4, perforated plates arranged perpendicular to the flow direction of the reactant and product stream. This cascading of the reactor greatly reduces backmixing in comparison with a simple bubble column and approximates plug flow behavior. As a result of this process engineering measure, both the yield and the selectivity of the hydroformylation can be improved.

Further preferred embodiments for carrying out the hydroformylation step a) are described, for example, in U.S. Pat. No. 6,723,884, incorporated herein by reference, and U.S. Pat. No. 6,720,457, incorporated herein by reference. Thus, according to U.S. Pat. No. 6,723,884, a substream of the liquid mixed phase (aqueous cobalt salt solution/organic phase) is taken off from the lower part of the reactor and is fed back in at a point higher up on the reactor. According to U.S. Pat. No. 6,720,457, the level of an aqueous phase is kept constant in the hydroformylation reactor. The concentration of cobalt compounds (calculated as metallic cobalt) in the aqueous bottom phase is preferably in the range from 0.4 to 1.7% by mass.

The process step a) is preferably carried out at a temperature of from 100 to 250° C., more preferably from 140 to 210° C. The pressure (synthesis gas pressure) at which process step a) is carried out is preferably from 10 to 40 MPa, more preferably from 20 to 30 MPa. The volume ratio of carbon monoxide to hydrogen in the synthesis gas is preferably from 2:1 to 1:2, more preferably from 1:1 to 1:1.5. The synthesis gas is preferably used in excess, for example in an amount up to three times the stoichiometric amount.

One or more process steps a) can be present in the process of the invention. If a plurality of hydroformylation steps a) are present in the process of the invention, identical or different conditions can be set in these process steps. In the case of multistage process variants, the hydroformylation in the first process stage, in which the reactive olefins are reacted, is preferably carried out at temperatures of from 140 to 195° C., more preferably from 160 to 185° C. In a first of a plurality of process stages, olefin conversions of from 20 to 95%, preferably from 50 to 80%, are preferably aimed at.

The concentration of cobalt compounds (calculated as metallic cobalt) in the liquid hydroformylation output is preferably from 0.01 to 0.5% by mass, more preferably from 0.02 to 0.08% by mass (based on the sum of organic and aqueous phases).

Due to the different possible ways of adding water, the water content in the input into the hydroformylation reactor can be determined only with difficulty. The water content in the output from the reactor may be virtually the same as the water content of the liquid phase during the reaction. The water concentrations of the liquid hydroformylation outputs can be from 0.1 to 10% by mass, in particular from 0.5 to 5% by mass. The water contents of the hydroformylation outputs from the individual hydroformylation stages can be identical or different. The water is preferably homogeneously dissolved in the liquid hydroformylation outputs.

The reactors in which the hydroformylation of step a) is carried out can, if a plurality of process steps a) are present, be identical or different in all process steps. Examples of reactor types which can be used are bubble column reactors, loop reactors, jet nozzle reactors, stirred reactors and tube reactors, some of which can be cascaded and/or provided with internals.

b) Catalyst Separation

To treat a hydroformylation mixture which, for example, has been obtained from a step a) according to step b) (cobalt removal), the product mixtures are, after leaving the hydroformylation reactors, preferably depressurized to from 1 to 3 MPa and reacted with oxygen-containing gases, in particular air or oxygen, in the presence of acidic, aqueous cobalt(II) salt solutions ("process water") and thus freed of cobalt carbonyl complexes by oxidation. Step b) is preferably carried out at a temperature of from 90 to 160° C., more preferably from 110 to 150° C. The hydroformylation-active cobalt carbonyl complexes are thus destroyed with formation of cobalt(II) salts. Cobalt removal processes are well known and are comprehensively described in the literature, e.g. by J. FALBE, in "New Syntheses with Carbon Monoxide", Springer Verlag (1980), Berlin, Heidelberg, New York, page 158 ff, incorporated herein by reference. The cobalt (II) salt solutions used preferably have a pH of from 1.5 to 4.5.

The treatment according to step b) is preferably carried out in a pressure vessel filled with packing elements, e.g. Raschig rings, in which very high exchange areas between the phases are produced.

c) Separation of the Mixture from b)

A mixture obtained according to step b), which comprises an organic phase which comprises aliphatic aldehydes and has been depleted in cobalt and a cobalt-rich aqueous phase, is separated in step c) into an aqueous phase and an organic phase, preferably in a separation vessel downstream of the pressure vessel of step b). The aqueous phase, viz. the "process water", which comprises the backextracted cobalt recovered from the organic phase in the form of cobalt acetate/formate, can be recirculated to step a) in its entirety or after discharge of a small proportion. The aqueous phase is preferably recirculated directly to the hydroformylation reactor of the respective process stage and can be used as starting material for the in-situ preparation of the cobalt catalyst complexes.

Part of the excess formic acid can optionally be removed before the process water is recirculated to step a). This can be effected, for example, by distillation. Another possibility is to decompose part of the formic acid, for example catalytically as described in U.S. Pat. No. 6,403,836, incorporated herein by reference. It is also possible to prepare the actual hydroformylation catalyst (e.g., $CO_2(CO)_8$ and/or $HCo(CO)_4$) from the cobalt salt solution obtained in the cobalt removal by precarbonylation and use this in step a).

d) Hydrogenation

The hydrogenation of an aldehyde-containing phase according to step d) can be carried out in the gas phase or in the liquid phase. The hydrogenation of step d) is preferably carried out as a liquid-phase hydrogenation. The liquid-phase hydrogenation is preferably carried out at a total pressure of from 0.5 to 10 MPa, more preferably from 1.5 to 5 MPa. A hydrogenation in the gas phase can also be carried out at low pressures, with correspondingly large gas volumes. If a plurality of hydrogenation reactors are used, the total pressures can be identical or different, but the pressures in the individual reactors should be within the specified pressure limits.

The temperature at which the hydrogenation of step d) is carried out is preferably from 120 to 220° C., particularly preferably from 140 to 180° C., in the liquid or gaseous phase. Examples of hydrogenations which can be used as step d) in the process of the invention are described, for example, in the patent applications U.S. Pat. No. 6,184,424, incorporated herein by reference, and U.S. Pat. No. 6,239,318, incorporated herein by reference.

In the process of the invention, the hydrogenation can optionally be carried out in the presence of water. The water required can be present in the feed to the reactor. However, it is also possible to feed in water at any point on the hydrogenation apparatus. When step d) is carried out as a gas-phase hydrogenation, water is advantageously introduced in the form of water vapor. A preferred hydrogenation process which can be used as step d) in the process of the invention is liquid-phase hydrogenation with addition of water, as is described, for example, in U.S. Pat. No. 6,680,414, incorporated herein by reference. The hydrogenation is preferably carried out at a water content of from 0.05 to 10% by mass, more preferably from 0.5 to 5% by mass and particularly preferably from 1 to 2.5% by mass. The water content is determined in the output from the hydrogenation.

As catalysts, it is possible to use the catalysts used in the abovementioned known processes. The hydrogenation of step b) is preferably carried out using, for example, copper, nickel, copper/nickel, copper/chromium, copper/chromium/nickel, zinc/chromium, nickel/molybdenum catalysts. The catalysts can be unsupported or the hydrogenation-active substances or their precursors can have been applied to supports, for example aluminum oxide, titanium dioxide, zirconium dioxide or silicon dioxide.

Preferred catalysts used in step d) comprise from 0.3 to 15% by mass of each of copper and nickel and also, as activators, from 0.05 to 3.5% by mass of chromium and preferably from 0.01 to 1.6% by mass, more preferably from 0.02 to 1.2% by mass, of an alkali component, e.g. sodium or potassium, on a support material, preferably aluminum oxide and silicon dioxide. The amounts indicated are based on the not yet reduced catalyst. The alkali component is optional.

The catalysts are advantageously used in a form in which they offer a low flow resistance, e.g. in the form of granules, pellets or shaped bodies such as tablets, cylinders, rod extrudates or rings. They are advantageously activated, e.g. by heating in a stream of hydrogen, before use.

f) Fractional Distillation

It can be advantageous for a step f) in which the organic phase obtained in step c) is separated, e.g. by a distillation, into a low-boiling fraction and an aldehyde-containing bottom fraction to be provided between the steps c) and d) in the process of the invention. The organic phase obtained after step c) can comprise unreacted olefins, aldehydes, alcohols, formic esters and high boilers and also traces of cobalt compounds. In step f), this phase is fractionated to give a fraction which comprises low boilers and, in particular, comprises the unreacted olefins and a bottom fraction which comprises, in particular, the desired products (aldehydes, alcohols and formates). The low boilers can be separated off from the hydroformylation products by, for example, distillation or steam distillation.

The low-boiling fraction (overhead fraction) may comprise unreacted olefins from step a) and may further comprise paraffins obtained by hydrogenation of olefins, dissolved water and possibly small amounts of desired products. The low-boiling fraction is preferably recirculated to a hydroformylation step. If a plurality of hydroformylation steps a) are present in various reaction stages, the low-boiling fraction from one hydroformylation step can be passed to the following reaction stage or be recirculated to the hydroformylation step of the last reaction stage.

The optional step f) can be carried out before or after step e). Step f) is preferably carried out before step e), so that the organic phase from step c) is separated in a distillation step f) into a low-boiling fraction and an aldehyde-containing bottom fraction and the aldehyde-containing bottom fraction is fed to step e). In this way, the amount of material sent to the adsorber is reduced.

The process of the invention can comprise one or more stages which each comprise one or more of the steps a), b), c), d), e) and, if desired, f), with each of the steps a) to e) being employed or carried out at least once in the totality of all stages in the process of the invention. The stages can, in particular, be arranged so that the steps d), e) and/or f) are only present once in the overall process, while the steps a) to c) are present in a plurality of stages, i.e. are present a number of times.

If the process of the invention is carried out in a single stage, all or part of the organic phase separated off in step c) can be passed to either process stage e) or f). Preference is given to passing on only part of the organic phase, so as to provide an outlet for the aliphatic compounds which would otherwise accumulate.

It can be advantageous for the process of the invention to be carried out in 2, 3, 4 or more than 4 stages. Each process stage and each process step of the process of the invention can be carried out continuously or batchwise. Preference is given to carrying out all process steps continuously.

Some embodiments of the process of the invention in which the process is carried out in a plurality of stages are described below, without the invention being restricted to these embodiments.

Embodiment 1

In this embodiment, at least two reaction stages are employed, with the low-boiling fraction separated off in step f) being passed to step a) of the following reaction stage and the aldehyde-containing bottom fractions separated off in the steps f) of all reaction stages being hydrogenated in a joint step d). In this process variant, the steps a), b), c) and f) are carried out in succession and only the step d), viz. the hydrogenation of the aldehyde fraction, is carried out jointly for all reaction stages.

One variant of embodiment 1 of the process of the invention is shown in the form of a block diagram in FIG. 1. Step a) is carried out in a first hydroformylation reactor 1 into which an olefin mixture 3, synthesis gas 2 (carbon monoxide and hydrogen) and an aqueous solution of a cobalt compound or cobalt catalyst and water 4 are fed. The hydroformylation mixture 5 obtained in this way is depressurized into the step b) and the depressurized hydroformylation mixture is treated with aqueous, acidic cobalt(II) salt solution and air in the vessel 7. The mixture obtained in the vessel 7 is freed of cobalt compounds 4 in the first catalyst separation 8 in step c). The depressurization gas 6 (synthesis gas which has not been consumed) is taken off upstream of the catalyst separation 8. The aqueous phase comprising cobalt compounds is recirculated to the first hydroformylation reactor 1, if appropriate after discharge of a small substream and replacement by fresh catalyst. For the present purposes, the term catalyst includes precursors of catalysts, e.g. cobalt(II) salt solutions. The organic phase 9 which has been freed of the catalyst goes from there to a distillation column 10 in which the separation step f) is carried out and the organic phase is separated into a low-boiling fraction 11, which comprises predominantly unreacted olefins, and crude aldehyde 12. The low boiler 11, synthesis gas 14 and an aqueous solution of a cobalt compound or a previously formed cobalt catalyst and water 16 are introduced into the second hydroformylation reactor 13 (step a) of the second stage). The hydroformylation mixture 15 from the second hydroformylation reactor 13 is once again depressurized and the depressurized hydroformylation mixture 15 is, after the second cobalt removal 18 (step b) of the second stage), freed of catalyst 16 in the second catalyst separation 19 (step c) of the second stage) and the catalyst 16 is in turn recirculated to the second hydroformylation reactor 13, if appropriate after discharge of a small substream and replacement by fresh catalyst. The depressurization gas 17 (synthesis gas which has not been consumed) is taken off upstream of the catalyst separation 19. The decatalyzed hydroformylation mixture 20 is fractionated in the distillation column 21 (step f) of the second stage) to give a low-boiling fraction 22, which comprises predominantly saturated hydrocarbons, and crude aldehyde 23. If appropriate, part of the low-boiling fraction 22 can be recirculated to the reactor 13. (Line not shown in FIG. 1). The bottom fractions (crude aldehyde) from the distillation columns 10 and 21 (step f) are combined and passed via an adsorber 28 (step e) to the hydrogenation unit 24 in which crude aldehyde is hydrogenated by means of hydrogen in process step d) to give the alcohol 25 which can optionally be worked up to produce pure alcohol in a distillation (not shown).

In this embodiment of the invention, each process stage comprises a hydroformylation step a), a cobalt removal step b), a catalyst separation step c) and a separation step f), with the proviso that the catalyst separated off in c) is recirculated directly or after work-up to the hydroformylation step a) of the respective process stage. In this process variant, it is also possible, as an optional alternative, for the second process stage to have no separation step f) and the hydroformylation mixture 20 to be conveyed directly via line 29 to the adsorber 28 to carry out process step e).

The separation according to the invention of small amounts of cobalt compounds from the organic phases or the aldehyde-containing fractions is possible at one or more points in this process variant. Thus, step e) can be carried out not only at the point where the adsorber 28 is provided, but step e) can also be carried out, additionally or in place of adsorber 28, after the two steps c) after the separation of the aqueous phase in 8 or 19 in the optional adsorbers 26 and 27 or after the separation of the aldehyde-containing bottom fraction from the low-boiling fraction in the distillation columns 10 and 21 in the optional adsorbers 30 and 31. The removal of small amounts of cobalt compounds according to step e) is preferably carried out only once, directly before the hydrogenation stage, i.e. in the adsorber 28.

Embodiment 2

In this embodiment of the process of the invention, two reaction stages are employed, with the low boilers separated off in step f) of the first reaction stage being passed to step a) of the second reaction stage and the organic output from step c) of both stages being passed to step f) of the first reaction stage. Here, each reaction stage comprises a hydroformylation step a), a cobalt removal step b) and a catalyst separation step c), with the catalyst phase which has been separated off being returned to the respective hydroformylation step. The organic phase which has been separated off is separated in a separation step f) common to both reaction stages into a low-boiling fraction and an aldehyde-containing subfraction. The low-boiling fraction obtained in this way is passed to the hydroformylation step a) of the second reaction stage, and the bottom fraction which has been separated off is passed to the adsorption step e) and subsequently the hydrogenation step d).

Figure 2:
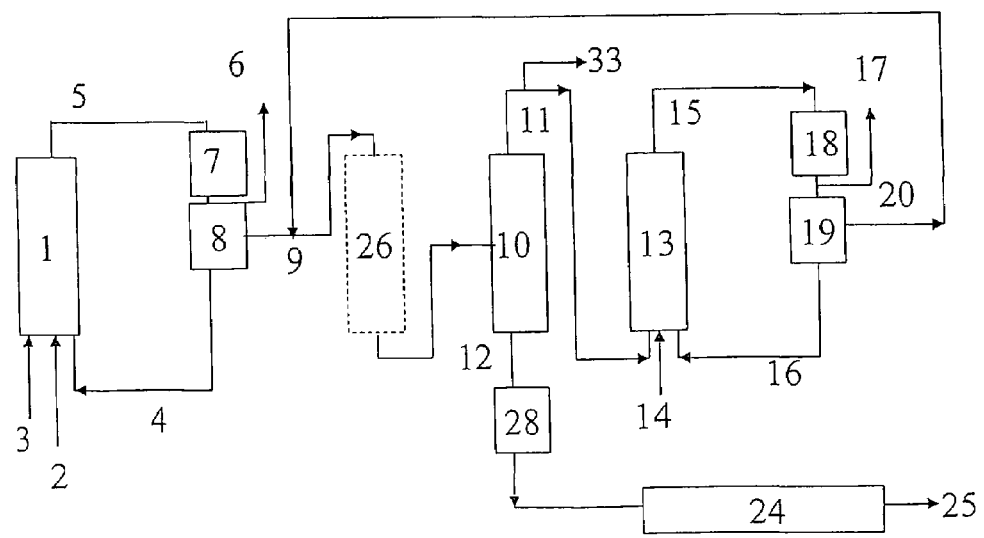
FIG. 2 shows another embodiment of the process for preparing aliphatic alcohols.

A block diagram of one variant of this embodiment of the process of the invention is shown in FIG. 2. An olefin mixture 3, synthesis gas 2 (carbon monoxide and hydrogen) and an aqueous solution of a cobalt compound or cobalt catalyst together with water are fed into the hydroformylation reactor 1 of the first process stage. The hydroformylation mixture 5 obtained in step a) of the first stage is depressurized, and the depressurized hydroformylation mixture is, after the treatment according to step b) carried out using aqueous, acidic cobalt(II) salt solution and air (cobalt removal) 7, freed of cobalt compounds 4 according to step c) in the first catalyst separation 8. The depressurization gas 6 (synthesis gas which has not been consumed) is taken off upstream of the catalyst separation 8. The aqueous phase comprising cobalt salts is recirculated to the first hydroformylation reactor 1, if appropriate after discharge of a small substream and replacement by fresh catalyst. The decobalted organic phase 9 obtained in the separation according to step c) is passed to the distillation column 10 (step f)). There, it is separated together with the decobalted hydroformylation mixture 20 from the second hydroformylation reactor 13 into a fraction 11, which comprises unreacted olefins and inert paraffins, and crude aldehyde 12. The low-boiling fraction 11 is, after discharge of a substream 33 to separate off saturated hydrocarbons (paraffins) and other, nonolefinic compounds, introduced together with synthesis gas 14 and an aqueous solution of a cobalt compound or a mixture 16 of cobalt catalyst and water into the second hydroformylation reactor 13 to carry out step a) of the second stage. The hydroformylation mixture 15 obtained in this way is depressurized and the depressurized hydroformylation mixture is, after a cobalt removal 18 according to step b), freed of the catalyst 16 according to step c) in the second catalyst separation 19, and the catalyst 16 is recirculated to the second hydroformylation reactor 13, if appropriate after discharge of a small substream and replacement by fresh catalyst. The depressurization gas 17 (synthesis gas which has not been consumed) is taken off upstream of the catalyst separation 19. The decobalted second hydroformylation mixture 20 is, as already mentioned, fed together with the hydroformylation mixture 9 from the first stage into the separation stage 10. The crude aldehyde 12 obtained as bottom fraction in the distillation column of step f) is freed of residual cobalt according to step e) in the adsorber 28 and subsequently hydrogenated by means of hydrogen in the hydrogenation unit 24 to give the crude alcohol 25. This alcohol can be worked up to produce the pure alcohol in a distillation (not shown).

Instead of or in addition to carrying out step e) in the adsorber 28, step e) can also be carried out in adsorber 26 after the organic phases 9 and 32 from the separation steps c) of the first and second stages have been combined and before they are fed into the distillation column 10 of step f).

The discharge of the saturated hydrocarbons can also be effected by work-up of a substream of the decobalted hydroformylation product 20 (not shown) instead of via the substream 33. This can be realized industrially by means of, for example, a fractional distillation of the substream to give low boilers which are discharged and aldehydes which are recirculated into the decobalted hydroformylation mixture 20 or the crude aldehyde 12.

This embodiment of the process of the invention has a hydroformylation step a), a cobalt removal step b) and a catalyst separation step c) for each process stage, with the combined liquid hydroformylation mixtures being separated into a low-boiling fraction and a bottom fraction in a joint distillation step f). The catalyst separated off in the steps c) can be recirculated to the respective process stage either directly or after work-up in the hydroformylation step a).

Embodiment 3

In this embodiment of the process of the invention, two reaction stages are employed, with the low boilers separated off in step f) of the first reaction stage being passed to step a) of the second reaction stage and the steps b), c) and d) being carried out jointly for the two reaction stages.

Figure 3:
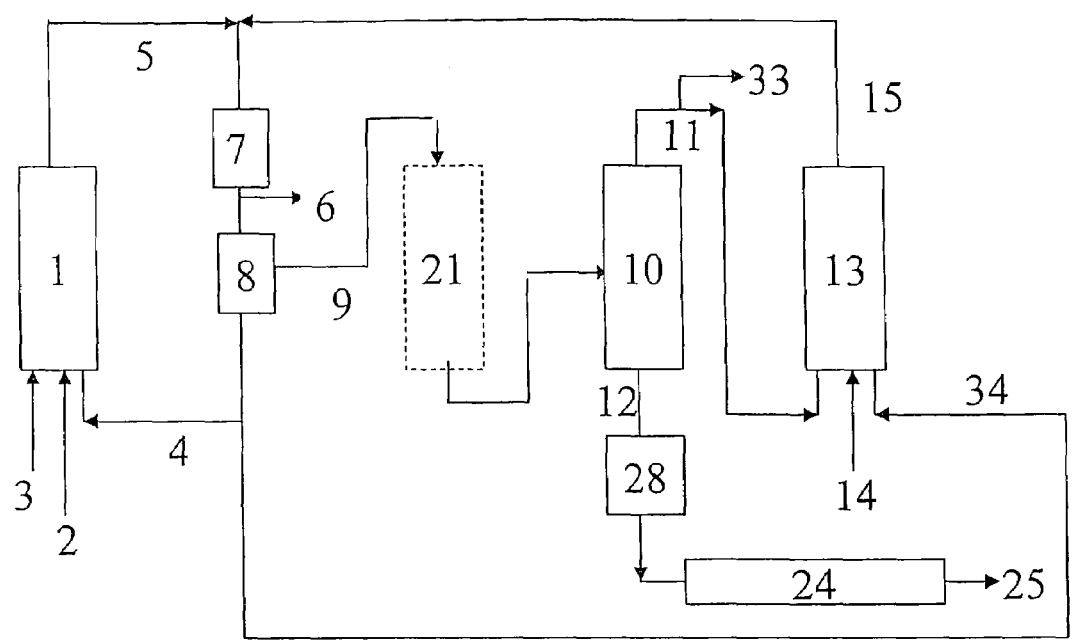
FIG. 3 shows a block diagram of one embodiment of the invention having two reaction stages.

One variant of this embodiment of the process of the invention is shown in the form of a block diagram in FIG. 3. An olefin mixture 3, synthesis gas 2 (carbon monoxide and hydrogen) and an aqueous solution of a cobalt compound or a mixture of cobalt catalyst and substream 4 are fed into the first hydroformylation reactor 1. The hydroformylation mixture 5 obtained in this way in step a) of the first reaction stage is depressurized together with the hydroformylation mixture 15 from the second hydroformylation reactor 13 (step a) of the second process stage) as combined hydroformylation outputs and, after the cobalt removal 7 (step b)), the organic phase is freed of the catalyst according to step c) in the catalyst separation 8. The synthesis gas 6 which has not been consumed is taken off upstream of the catalyst separation 8. A mixture 9 comprising the aldehydes formed, alcohols and unreacted olefins is obtained. The catalyst is, if appropriate after discharge of a proportion and replacement by fresh catalyst, divided into the two substreams 4 and 34. Substream 4 is recirculated to the hydroformylation reactor 1 of the first process stage and substream 34 is recirculated to the hydroformylation reactor 13 of the second process stage. The decobalted hydroformylation output 9 is fractionated in the distillation column 10 of process step a) to give the low-boiling fraction 11 and the crude aldehyde (bottom fraction) 12. The low-boiling fraction 11, which comprises the unreacted olefins, is, if appropriate after discharge of a proportion 33 to separate off saturated hydrocarbons or other nonolefinic compounds, introduced together with synthesis gas 14 and an aqueous solution of a cobalt compound or a mixture of cobalt catalyst and water 34 into the second hydroformylation reactor 13 (step a) of the second process stage). The crude aldehyde 12 is largely freed of cobalt in step e) in the adsorber 28 and can subsequently be hydrogenated by means of hydrogen in the hydrogenation unit 24 to give the crude alcohol 25. This can once again be worked up to produce pure alcohol in a distillation (not shown).

Instead of or in addition to carrying out the step e) in the adsorber 28, step e) can also be carried out in adsorber 21 before the organic phases 9 are fed into the distillation column 10 of step f).

In this embodiment of the process of the invention too, it is possible to carry out the discharge of saturated hydrocarbons via a separate work-up of a substream of the hydroformylation mixture 15, for example by separating off the low boilers by distillation.

In this third embodiment of the process of the invention, the combined reactor outputs of all hydroformylation steps a) go through only one cobalt removal b) and one catalyst separation step c) and one olefin separation step f). The catalyst separated off in process step c) is divided either directly or after a work-up and recirculated to the hydroformylation steps a) of the individual process stages.

The following examples illustrate the invention without restricting its scope which is defined by the claims and the description.

EXAMPLE 1

2 l of hydrogenation catalyst H 14154 (supplier: Degussa AG, Dusseldorf) (1400 g), which was in the form of cylindrical extrudates having a diameter of 1.2 mm and a length of from 2 to 10 mm, were placed in an adsorber (tube having an internal diameter of 50 mm). The length of the adsorber zone was thus 102 cm. A hydroformylation mixture from an isononanal plant having a content of cobalt compounds (expressed as cobalt) of 75 ppb by mass ($75*10^{-9}$ g/g) was pumped through the vertical adsorber at a superficial velocity of 61 m/h, which corresponds to a volume flow in the empty tube of about 110 l/h. The adsorber was operated at a temperature of 70° C. and at 3.1 MPa. The flow through the adsorber was from the top downward.

After 283 m³ of hydroformylation mixture had flowed through the adsorbent, the adsorber was opened and the entire adsorbent was taken out in eight column sections without cross-mixing. The position within the adsorption column and a mean bed length, distance from the surface of the inflow side, could be assigned to each column section. Each of the eight samples was dried, homogenized and the cobalt concentrations of each of them was subsequently determined spectroscopically (AAS), and the absolute amount of cobalt in each column section and the average specific loading (gram of cobalt per gram of adsorbent used) was then calculated. These values are shown in Table 1 below.

TABLE 1

Results of the evaluation of Example 1

| Number of the column section | Bed section in cm | Mean bed length in cm | Specific cobalt loading in g/g | Absolute quantity of cobalt in g |
|---|---|---|---|---|
| 1 | 0–2 | 1 | 0.0185 | 0.508 |
| 2 | 2–4 | 3 | 0.0199 | 0.545 |
| 3 | 4–8 | 6 | 0.0157 | 0.863 |
| 4 | 8–24 | 16 | 0.0193 | 4.236 |
| 5 | 24–42 | 33 | 0.0135 | 3.345 |
| 6 | 42–62 | 52 | 0.0110 | 3.032 |
| 7 | 62–93 | 77.5 | 0.0050 | 2.122 |
| 8 | 93–102 | 97.5 | 0.0047 | 0.581 |
| | | | Total | 15.322 |

Cobalt compounds containing a total of 17.025 g of cobalt were introduced into the adsorber with the hydroformylation mixture during the experiment. Thus, 15.322 g were adsorbed. This corresponds to a retention of 90%. The cobalt content of the raffinate was only 7.5 ppb by mass. The experiment thus showed that the cobalt content could be significantly reduced with a little outlay even in the trace range by adsorption under industrial conditions. A similarly good result is obtained when a hydrogenation catalyst which is no longer suitable as hydrogenation catalyst because of unsatisfactory activity is used.

EXAMPLE 2

The same apparatus as in Example 1 was used. It was charged with 2 l of activated carbon from Chemviron. To carry out the adsorption, the same feed flowed through the adsorption tube at the same space velocity and the same temperature. After 647 m³ (519 t) of the hydroformylation mixture had been passed through the tube, the amount of cobalt on the total adsorbent was determined. This was 3.3 g.

EXAMPLE 3

Example 3 was carried out in a manner analogous to Example 2. The adsorbent used was silicon dioxide KC-Siliperl AF 125 from Kalichemie. After 1060 m³ (850 t) of hydroformylation mixture had been passed through the tube, 1.6 g of cobalt had been adsorbed.

The three examples show that the cobalt content of hydroformylation mixtures containing cobalt compounds in the trace range (ppb concentration range) can be reduced by adsorption. An adsorbent which is particularly well-suited for this purpose is the hydrogenation catalyst H 14154, which has an $Al_2O_3$ support.

German application no. 10 2004 059292.6 filed on Dec. 9, 2004 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A process for preparing aliphatic alcohols having from 7 to 25 carbon atoms, comprising:
   a) hydroformylating one or more olefins having from 6 to 24 carbon atoms in the presence of one or more cobalt catalysts to form a hydroformylation mixture comprising the hydroformylated olefins and the cobalt catalysts;
   b) treating the hydroformylation mixture with one or more oxygen-containing gases in the presence of an acidic, aqueous cobalt(II) salt solution to form a treated mixture;
   c) separating the treated mixture into an aqueous phase comprising cobalt salts and an organic phase comprising one or more aliphatic aldehydes;
   d) hydrogenating the aldehyde-containing organic phase; and
   e) prior to the hydrogenating, treating at least a part of the aldehyde-containing organic phase with at least one adsorbent to remove at least a portion of the cobalt compounds from the organic phase.

2. The process as claimed in claim 1, wherein the adsorbent is at least one selected from the group consisting of aluminum oxide, silicon oxide, an aluminosilicate, an activated carbon and a material comprising one or more thereof.

3. The process as claimed in claim 1, wherein the adsorbent is at least one of an exhausted hydrogenation catalyst and a fresh hydrogenation catalyst.

4. The process as claimed in claim 3, wherein the hydrogenating d) is carried out with at least one hydrogenation catalyst comprising at least one of aluminum oxide, silicon oxide, an aluminosilicate and an activated carbon, as a support material.

5. The process as claimed in claim 1, wherein the treating e) is carried out at a temperature of from 5 to 250° C.

6. The process as claimed in claim 1, wherein the treating e) is carried out at a pressure of from 0.1 to 20 MPa.

7. The process as claimed in claim 1, wherein the treating e) is carried out with or without addition of hydrogen.

8. The process as claimed in claim 1, wherein the treating e) is carried out within or outside a reactor in which the hydrogenating d) is carried out.

9. The process as claimed in claim 1, wherein the treating e) is carried out in an adsorber or a plurality of adsorbers.

10. The process as claimed in claim 9, wherein treating e) is carried out in two adsorber units connected in parallel, wherein each adsorber unit is capable of containing one or more adsorbers.

11. The process as claimed in claim 9, wherein the treating e) is carried out in an apparatus in which at least two adsorber units connected in parallel are present and the two adsorber units are operated alternately.

12. The process as claimed in claim 11, further comprising:
replacing or regenerating an adsorbent in an adsorber unit which is not currently in operation.

13. The process as claimed in claim 1, further comprising:
g) removing a part of the cobalt in the mixture fed to the treating e) by single-stage or multiple extraction with water before the treating e).

14. The process as claimed in claim 1, further comprising:
f) separating the organic phase formed by the separating c) into a low-boiling fraction and an aldehyde-containing bottom fraction by distillation and passing the aldehyde-containing bottom fraction to the treating e).

15. The process as claimed in claim 1, carried out in the following order: a), b), c), d), then e).

16. The process as claimed in claim 1, wherein one or more of a)–d) is carried out more than one time before e) is carried out.

* * * * *